(12) United States Patent
Ayyappanpillai et al.

(10) Patent No.: US 9,493,488 B2
(45) Date of Patent: Nov. 15, 2016

(54) CARBAZOLE END CAPPED BIPYRIDINE COMPOUNDS AND PROCESS FOR PREPARATION THEREOF

(75) Inventors: Ajayaghosh Ayyappanpillai, Pappanamcode Thiruvananthapuram (IN); Divya Kizhumuri, Pappanamcode Thiruvananthapuram (IN); Srinivasan Sampath, Pappanamcode Thiruvananthapuram (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/985,085

(22) PCT Filed: Feb. 14, 2012

(86) PCT No.: PCT/IB2012/050656
§ 371 (c)(1),
(2), (4) Date: Oct. 7, 2013

(87) PCT Pub. No.: WO2012/110945
PCT Pub. Date: Aug. 23, 2012

(65) Prior Publication Data
US 2014/0023883 A1     Jan. 23, 2014

(30) Foreign Application Priority Data
Feb. 14, 2011 (IN) .............................. 367/DEL/2011

(51) Int. Cl.
*C07D 401/14* (2006.01)
*C07F 3/06* (2006.01)

(52) U.S. Cl.
CPC ............... *C07F 3/06* (2013.01); *C07D 401/14* (2013.01)

(58) Field of Classification Search
CPC .................................................. C07D 401/14
USPC ....................................................... 546/256
See application file for complete search history.

(56) References Cited

U.S. PATENT DOCUMENTS

| | | |
|---|---|---|
| 5,770,737 A | 6/1998 | Reinhardt et al. |
| 6,548,836 B1 | 4/2003 | Rubner et al. |
| 6,600,175 B1 | 7/2003 | Baretz et al. |
| 6,670,052 B2 | 12/2003 | Hirose et al. |
| 6,713,781 B1 | 3/2004 | Chen et al. |
| 7,179,542 B2 | 2/2007 | Chen et al. |
| 7,253,287 B1 | 8/2007 | Belfield et al. |
| 7,763,439 B2 | 7/2010 | Meltola et al. |

FOREIGN PATENT DOCUMENTS

| | | |
|---|---|---|
| CN | 101538416 A | 9/2009 |
| WO | 2009/084007 A1 | 7/2009 |
| WO | 2011/033531 A1 | 3/2011 |

OTHER PUBLICATIONS

Liu, at al., "A Series of Carbazole Cationic Compounds with Large Two-Photon Absorption Cross Sections for Imaging Mitochondria in Living Cells with Two-Photon Fluorescence Microscopy," *Journal of Fluorescence*, Oct. 16, 2010, vol. 21, No. 2, pp. 497-506.
Pei, et al., "Structural Dependence of the Selectivity of Fluorescent Chemosensors to $Mg^{2+}$ from Alkali Earth Metal Ions," *Macromolecular Rapid Communications*, Jan. 1, 2002. vol. 23, No. 1, pp. 21-25.

*Primary Examiner* — Patricia L Morris
(74) *Attorney, Agent, or Firm* — DLA Piper LLP (US)

(57) ABSTRACT

The present invention is to provide highly solid state emissive fluorophores of the formula 1 and 2 useful for the solid state lighting. The formula 1 and 2 have good solid state emission in blue and green region respectively. The zinc complexes of formula 1A and 2A have yellow and red emission respectively in solid state. The present invention also provide high solid state emissive assay of formula 1 and 2 to convert UV light into visible light by coating the color tunable materials on the 365-nm emitting solid state LED. The present invention further provides carbazole end-capped bipyridine for screening of metal salts with different counterions in solutions. The discrimination of the various metal salts can be monitored by noting the fluorescence change in solution. The zinc salts with different counterions have different emission color in solution. The present invention also develop a new two photon active fluorescent $Zn^{2+}$ specific probe for detecting $Zn^{2+}$ in cellular environments. Assay with formula 3 is used as a fluorescent probe for two photon imaging of $Zn^{2+}$ ions in HeLa cells. The high two photon absorption cross section and fluorescence quantum yield of formula 3 made it as a useful probe for detecting $Zn^{2+}$ in cellular environment by two photon excited fluorescence imaging.

2 Claims, 7 Drawing Sheets

CARBAZOLE END CAPPED BIPYRIDINE COMPOUNDS AND PROCESS FOR PREPARATION THEREOF

FIELD OF THE INVENTION

The present invention relates to Carbazole end capped bipyridine compounds of general formula A and their Zn-complex useful for solid state lighting, screening of counteranions and two photon biological imaging.

General formula A

The present invention also provides a process for the preparation of general formula A.

BACKGROUND OF THE INVENTION

The search for the development of tunable organic fluorophores with improved properties are of great interest. Fluorophores with attractive and efficient emission characteristics are desirable for applications in biological science, material science application such as organic light emitting diodes (OLEDs) and sensing applications. Reference may be made to: a) E. M. Nolan, S. J. Lippard, Chem. Rev. 2008, 108, 3443; b) Applied Fluorescence in Chemistry, Biology, and Medicine (Eds.: W. Rettig, B. Strehmel, S. Schrader, H. Seifert), Springer, New York, 1999; c) A. C. Grimsdale, K. L. Chan, R. E. Martin, P. G. Jokisz, A. B. Holmes, Chem. Rev. 2009, 109, 897; d) S. M. Kelly in Flat Panel Displays: Advanced Organic Materials (Ed.: J. A. Connor), The Royal Society of Chemistry, Cambridge, 2000; e) S. Park, J. E. Kwon, S. H. Kim, J. Seo, K. Chung, S.-Y. Park, D.-J. Jang, B. M. Medina, J. Gierschner, S. Y. Park, J. Am. Chem. Soc. 2009, 131, 14043; f) Y. Yamaguchi, Y. Matsubara, T. Ochi, T. Wakamiya, Z.-I. Yoshida, J. Am. Chem. Soc. 2008, 130, 113867; g) Z. M. Hudson, S. Wang, Acc. Che. Res. 2009, 42, 1584; g) H. S. Joshi, R. Jamshidi, Y. Tor, Angew. Chem. Int. Ed. 1999, 38, 2722;

A critical element in designing and fabricating such materials is the control of their emission wavelength. Blue-, green- and red-light-emitting materials are needed for full-color displays. For organic molecules this is often achieved by chemically modifying the π-conjugation or the substituent group; which include substitution with stronger donor or acceptor moieties. This will effectively modulate the HOMO-LUMO gap of the molecules. An alternative approach for controlling the emitted color of organic materials is to append fluorescent chromophores to a polymeric backbone or to blend such dyes into inert polymeric matrices. Reference may be made to: a) Y. Yamaguchi, T. Tanaka, S. Kobayashi, T. Wakamiya, Y. Matsubara, Z.-I. Yoshida, J. Am. Chem. Soc. 2005, 127, 9332; b) R. Abbel, C. Grenier, M. J. Pounderoijen, J. W. Stouwdam, P. E. L. G. Leclere, R. P. Sijbesma, E. W. Meijer, A. P. H. J. Schenning, J. Am. Chem. Soc. 2009, 131, 833; c) G. Kwak, H. Kim, I.-K. Kang, S.-H. Kim, Macromolecules, 2009, 42, 1733.

Light emitting devices can be used in displays (eg., flat-panel displays), screens such as computer screens and other items that require illumination. The brightness of the light emitting device is an important feature of the device. Solid state light emitting devices including LED's are extremely useful because of their low fabrication costs and long term durability. Reference may be made to: Rubner et al. U.S. Pat. No. 6,548,836, Baretz et al. U.S. Pat. No. 6,600,175. As the organic luminescent material, organic dyes emitting fluorescence such as 8-quinolinol aluminium complex or coumarin compounds are used. Although the organic light emitting diode has high luminescent characteristics, they involve a problem in the stability upon light emission or half life. Reference may be made to: Hirose et al. U.S. Pat. No. 6,670,052

An organic light-emitting device in which an oxazole-, thiazole- or imidazole-fused phenanthroline molecule is used as an emissive layer by Chen et al. U.S. Pat. No. 7,179,542, U.S. Pat. No. 6,713,781.

So far, a variety of strategies have been worked out to realize high solid state emission. The modulation of optical-band gap by changing the strength of donor-acceptor have been shown by Ajayaghosh and coworkers. Reference can be made to: a) A. Ajayaghosh, V. K. Praveen, S. Srinivasan, and R. Varghese, Adv. Mater. 2007, 19, 411; b) C. Vijayakumar, V. K. Praveen, and A. Ajayaghosh Adv. Mater. 2009, 21, 2059, Ajayaghosh et al. PCT/IN2008/000372. Recently the emission of the three primary colors (blue, green and red) simultaneously with equal intensities to produce white light and the pure colors separately in a tunable way was achieved from a single component emitter. Reference can be made to: G. He, D. Guo, C. He, X. Zhang, X. Zhao, and C. Duan; Angew. Chem. Int. Ed. 2009, 48, 6132.

But the rational design of fluorescent probes with appreciable quantum yield in solid state is still a challenging task. Therefore the demand for the design and development of efficient fluorescent materials are always a matter of scientific concern. In the present invention we put forward a simple and easy protocol for developing organic luminescent materials with high solid-state emission useful for fabricating multicolor light emitting devices. The conversion of UV light into visible light is also demonstrated by coating the color tunable materials on the 365-nm emitting solid state LED.

Another application f fluorophores is for sensing of cations, anions and neutral molecules. Reference can be made to: a) A. P. de Silva, H. Q. Gunaratne, T. Gunnlaugsson, A. J. M. Huxely, C. P. McCoy, J. T. Rademacher, T. E. Rice, Chem. Rev. 1997, 97, 1515; b) M. Takeuchi, M. Ikeda, A. Sugasaki, S. Shinkai, Acc. Chem. Res. 2001, 34, 865; c) A. Ajayaghosh, Acc. Chem. Res. 2005, 38, 449; d) E. L. Que, D. W. Domaille, C. J. Chang, Chem. Rev. 2008, 108, 1517; e) E. Nolan, S. J. Lippard, Chem. Rev. 2008, 108, 3443; f) R. McRae, P. Bagchi, S. Sumalekshmy, C. J. Fahrni, Chem. Rev. 2009, 109, 4780; g) E. J. O'Neil, B. D. Smith, Chem. Soc. Rev. 2006, 250, 3068; h) S. W. Thomas III, G. D. Joly, T. M. Swager, Chem. Rev. 2007, 107, 1339.

Many of these sensors are specific either for a particular cation or anion. However, screening of a specific metal salts in terms of the associated counter anions remains challenging. For example, colorimetric and/or fluorimetric probes that sense a specific cation will not in general be able to differentiate the associated counteranions and vice-versa. Fluorophores with strong intramolecular charge transfer (ICT) shows substantial changes in fluorescence with respect to the surrounding environment (solvatochromic probes). One of the methods to impart solvatochromic property to a fluorophore is by functionalization with electron donor (D) and electron acceptor (A) moieties. Such a structure will cause significant variation in the dipole moment of the molecule between the ground state and excited state. If the donor and the acceptor moieties are weak, charge transfer occurs in the excited state thereby perturbing the fluorescence. Fluorophores with positive solvatochromism show red-shift in the emission maximum with low quantum yields on increasing the solvent polarity. In addition, solvatochromic probes will also be associated with change in fluorescence lifetime with respect to solvent polarity. Therefore, solvatochromic probes have been widely used for a variety of applications such as polarity sensitive live cell imaging, cation sensing, and for biosensing. However, solvatochromic fluorescence property has not been exploited for differentiating and identifying the counter anions involved in different salts of a specific cation. In the present invention we show that the fluorescent molecular probe of formula 2 is able to distinguish zinc salts with various counterions. Reference may be made to: a) Sunahara, H.; Urano, Y.; Kojima, H.; Nagano, T *J. Am. Chem. Soc.* 2007, 129, 5597; b) S. Maruyama, K. Kikuchi, T. Hirano, Y. Urano, T. Nagano, *J. Am. Chem. Soc.* 2002, 124, 10650; c) S. Sumalekshmy, M. M. Henary, N. Siegel, P. V. Lawson, Y. Wu, K. Schmidt, J.-L. Bredas, J. W. Perry, C. J. Fahrni, *J. Am. Chem. Soc.* 2007, 129, 11888.

Certain fluorescence probes are highly fluorescing when excited with one photon at a wavelength in UV or visible range. However such wavelengths are inconvenient for cell imaging and tissue imaging because of their low penetration power and also due to the absorption of tissues and cells at this wavelength. Such wavelength also result in significant autofluorescence and phototoxicity. In order for the probe to be used as a two photon imaging probe for cells, it should be specific for a particular analyte, have cell viability, and it should have good two photon absorption cross section.

Many of the two photon absorbing compounds satisfy the formula D-π-D, A-π-A, D-A-D and A-D-A, wherein D is an electron donor group, A is an electron acceptor group and π comprises a bridge of π-conjugated bonds connecting the donor and acceptor. Molecules with these forms can be designed to operate in methods where in the compounds undergo simultaneous two photon absorption. Asymmetric dyes with large two photon absorption cross section are prepared by Reinhardt et al. Reference may be made to: U.S. Pat. No. 5,770,737.

Novel two photon probe with high fluorescence quantum yield, high two photon absorption cross section and high photostability are used in a method of multi photon imaging. In that, the fluorophores are functionalized with moieties having the properties of covalent attachment onto proteins, antibodies, DNA and RNA. The two photon dyes with high fluorescence intensity in the environment of cell membranes useful for distinguising hydrophilic and hydrophobic domains of the cell membranes are utilized for the real-time imaging of lipid rafts. Reference may be made to: Belfield et al. U.S. Pat. No. 7,253,287, Cho et al. U.S. Pat. No. 7,511,167. Dipyrromethaneboron difluoride dyes and their conjugates used in bioanalytical assays that are based on two-photon excitation. Reference can be made to: Meltola et al. U.S. Pat. No. 7,763,439.

OBJECTIVES OF THE INVENTION

The main object of the present invention is to provide Carbazole end capped bipyridine compounds of general formula A useful for solid state lighting and related applications.

Another object of the present invention is to provide a process for the preparation of Carbazole end capped bipyridine compounds of general formula A.

Another object of the present invention is to use the high solid state emissive assay powder of general formula A to convert UV light into visible light by coating the color tunable materials on the 365-nm emitting solid state LED.

Another object of the present invention is to provide a fluorophore of formula 2 for screening of metal salts with different counterions in solutions.

Yet another main objective of the present invention is to develop a new two photon active fluorescent $Zn^{2+}$ specific probe for detecting $Zn^{2+}$ in cellular environments. The present invention aims to use $Zn^{2+}$ specific fluorophore with formula 3 for two photon imaging of $Zn^{2+}$ ions in cellular environments.

SUMMARY OF THE INVENTION

Accordingly, the present invention relates to carbazole end capped bipyridine compounds of general formula A and its zinc complex of general formula B In one embodiment of the present invention the structural formulae of the representative compounds are:

R = —C₁₀H₂₁

4,4′-bis((E)-2-(9-decyl-9H-carbazol-3-yl)vinyl)-2,2′-bipyridine.

R = —C₁₀H₂₁

5,5′-bis((E)-2-(9-decyl-9H-carbazol-3-yl)vinyl)-2,2′-bipyridine.

R = —C₁₀H₂₁

Zinc complex of 4,4′-bis((E)-2-(9-decyl-9H-carbazol-3-yl)vinyl)-2,2′-bipyridine

-continued (2A)

R = —C₁₀H₂₁

Zinc complex of 5,5'-bis((E)-2-(9-decyl-9H-carbazol-3-yl)vinyl)-2,2'-bipyridine

In another embodiment of the present invention the compounds of general formula A and its Zinc complex of general formula B are useful for conversion of UV light to visible light in solid state.

In another embodiment of the present invention the compounds 1 and 2 are useful for conversion of UV light to blue color (490 nm) and green color (500 nm) in solid state respectively.

In another embodiment of the present invention the zinc complex 1A and the zinc complex 2A convert UV light to yellowish orange light (586 nm) and red light (622 nm) respectively.

In another embodiment of the present invention the compound 2 is useful for the identification of counteranion in zinc salts in solution state.

In another embodiment of the present invention solvent used in solution state is chloroform.

In another embodiment of the present invention the counteranions of zinc salts is selected from the group consisting of chloride, acetate, bromide, perchlorate, nitrate and triflate.

In another embodiment of the present invention a process for the preparation of compounds of general formula A and its Zinc complex of general formula B, wherein the said process comprising the steps;
 a. adding substituted bipyridine and substituted carbazole monoaldehyde in mole ratio 1:2 into a solvent in the presence of a base;
 b. stirring the reaction mixture as obtained in step (a) at temperature ranging between 32-40° C. for a period ranging between 12-14 h;
 c. cooling the reaction mixture as obtained in step (b) to obtain precipitate followed by dissolving precipitate in a solvent and subsequently evaporating solvent to obtain crude product;
 d. purifying the crude product as obtained in step (c) by column chromatography in basic alumina using petroleum ether as solvent to obtain pure compounds of general formula A.
 e. reacting the compound of general formula A with ZnCl₂ in mole ratio 1:1 in a solvent preferably acetonitrile at room temperature ranging between 30-35° C. to obtain the zinc complex of formula B.

In another embodiment of the present invention solvent used in step (a) is selected from the group consisting of dry DMF or dry THF.

In another embodiment of the present invention base used in step (a) is selected from the group consisting of potassium tertiary butoxide and sodium hydride.

In another embodiment of the present invention substituted bipyridine used in step (a) is selected from group consisting of tetraethyl 2,2'-bipyridine-5,5'-diylbis(methylene)diphosphonate and 4,4'-dimethyl-2,2'-bipyridine.

In another embodiment of the present invention substitute carbazole monoaldehyde used in step (a) is 9-substituted carbazole-2-carbaldehyde.

In another embodiment of the present invention yield of Carbazole end capped bipyridine compounds is in the range of 40-50%.

In another embodiment of the present invention a solid state emitting device prepared by using compound of general formula A and its zinc complex of general formula B, wherein process steps comprising;
 a) melting compounds of general formula A and its zinc complex of general formula B on a mortar by heating up to 200-210° C.;
 b) coating of said melt as obtained in step (a) over UV LED and allowed to cool for 15-20 minutes to prepare a solid state emitting device.

In another embodiment of the present invention solid state emitting device shows a solid state fluorescence quantum yield in the range of 4.3% to 45.6%.

In another embodiment of the present invention Use of compound of formula 3 for two Photon Imaging of zinc ions in biological cells selected from the group consisting of HeLa cell, Human muscle cells.

(formula 3)

5,5'-bis((E)-2-(9-(2-(2-(2-methoxyethoxy)ethoxy)ethyl-9H-carbazol-3-yl)vinyl)-2,2'-bipyridine

BRIEF DESCRIPTION ABOUT THE DRAWINGS

These and other features, aspects, and advantages of the present invention will become better understood with reference to the following description and appended claims and accompanying drawings where:

DETAILED DESCRIPTION OF THE INVENTION

The present invention is to provide highly solid state emissive fluorophores of formula 1 and 2 useful for the solid state lighting. The formula 1 and 2 have good solid state emission in blue and green region respectively. The zinc complexes of formula 1 and 2 have yellow and red emission respectively in solid state. The present invention also provide high solid state emissive assay of formula 1 and 2 to convert UV light into visible light by coating the color tunable materials on the 365-nm emitting solid state LED. The present invention further provides carbazole end-capped bipyridine for screening of metal salts with different counterions in solutions. The discrimination of the various metal salts can be monitored by noting the fluorescence change in solution. The zinc salts with different counterions have different emission color in solution. The present invention also develop a new two photon active fluorescent $Zn^{2+}$ specific probe for detecting $Zn^{2+}$ in cellular environments. Assay with formula 3 is used as a fluorescent probe for two photon imaging of $Zn^{2+}$ ions in HeLa cells. The high two photon absorption cross section and fluorescence quantum yield of formula 3 made it as a useful probe for detecting $Zn^{2+}$ in cellular environment by two photon excited fluorescence imaging.

R = —$C_{10}H_{21}$

-continued

2; R = —C$_{10}$H$_{21}$
3; R = —(CH$_2$—CH$_2$—O)$_3$—CH$_3$

R = —C$_{10}$H$_{21}$

Zinc complex of 4,4'-bis((E)-2-(9-decyl-9H-carbazol-3-yl)vinyl)-2,2'-bipyridine

R = —C$_{10}$H$_{21}$

Zinc complex of 5,5'-bis((E)-2-(9-decyl-9H-carbazol-3-yl)vinyl)-2,2'-bipyridine

EXAMPLES

The following examples are given to illustrate the process of the present invention and should not be construed to limit the scope of the present invention.

Example-1

Preparation of Formula 1

2 mmol of 4 (4,4'-dimethyl-2,2'-bipyridine) was dissolved in dry DMF (50 mL). Potassium tertiary butoxide (290 mg, 12 mmol). was added to the solution and stirred well. 6 mmol of the carbazole monoaldehyde (9-substituted carbazole-2-carbaldehyde) (5) was added to the reaction mixture. Then the reaction was stirred at room temperature (32° C.) for 12 h. After completion of the reaction the entire reaction mixture was poured to ice. The yellow precipitate formed was dissolved in chloroform (100 mL) and concentrated. The crude product was purified by column chromatography in basic alumina using petroleum ether as solvent. 1: mp 195-197° C.; (Yield: 40%)

$^1$H NMR (300 MHz, CDCl$_3$, δ): 8.70 (d, 2H, Ar H), 8.60 (d, 2H, Ar H), 8.30 (d, 2H, Ar H), 8.15-8.13 (d, 2H, Ar H), 7.74 (d, 1H, Ar H), 7.72 (s, 2H, Ar H), 7.67 (s, 1H, Ar H), 7.51-7.40 (m, 7H, Ar H), 7.29 (m, 2H, vinylic H), 7.21 (s, 2H, vinylic H), 7.16 (s, 1H, vinylic H), 4.33-4.29 (t, J=12 Hz, 4H; —NCH$_2$), 1.89 (m, 4H; CH$_2$), 1.35-1.24 (m, 28H; CH$_2$), 0.89 (m, 6H; CH$_3$).

$^{13}$C NMR (75 MHz, THF-d$^8$, δ): 154.85, 147.33, 144.30, 139.13, 138.95, 132.13, 123.77, 122.85, 121.37, 121.08, 118.38, 118.21, 117.52, 117.06, 115.53, 107.07, 40.82, 29.97, 27.65, 27.09, 25.27, 20.69, 11.58; IR (KBr): v=3047, 2920, 2848, 1622, 1581, 1492, 1467, 1377, 1355, 1332, 1238, 1143, 964, 866, 823, 752, 613; FAB-MS (m/z): [M+H]$^+$ calcd for $C_{58}H_{67}N_4$, 819.53. found, 820.38.

Example-2

Preparation of Formula 2

A suspension of sodium hydride (12 mmol, 290 mg) in dry THF (50 mL) was added slowly to a solution of the bisphosphonate (tetraethyl 2,2'-bipyridine-5,5'-diylbis (methylene)diphosphonate) (6) 912 mg) (2 mmol) and the carbazole aldehyde (5,9-substituted carbazole-2-carbaldehyde) (4 mmol, 1.35 g) in THF 50 mL). After refluxing for 12 h, at 65° C. the reaction mixture obtained was cooled followed by the is removal of the THF under reduced pressure to give a yellow solid residue. The residue was suspended in water 100 mL) and extracted with dichloromethane 50 mL). The organic layer was washed with brine 50 mL) dried over $Na_2SO_4$ and concentrated to give the crude product, which was further purified by column chromatography over basic alumina using petroleum ether as eluent. 2: mp 169-172° C.; Yield: 50%

$^1$H NMR (300 MHz, $CDCl_3$, δ): 8.82 (s, 2H, Ar H), 8.44-8.42 (d, 2H, Ar H), 8.28 (s, 2H, Ar H), 8.17-8.15 (d, 2H, Ar H), 8.03-8.01 (d, 2H, Ar H), 7.72-7.70 (d, 2H, Ar H), 7.52-7.40 (m, 8H, Ar H), 7.30-7.27 (d, 2H, vinylic, J=15 Hz), 7.19-7.16 (d, 2H, vinylic, J=15 Hz), 4.32-4.29 (t, 4H—$NCH_2$, J=15 Hz), 1.90 (m, 4H; $CH_2$), 1.66 (s, 4H, $CH_2$,), 1.40-1.37 (m, 24H; $CH_2$), 0.90-0.88 (t, 6H; $CH_3$).

$^{13}$C NMR (75 MHz, $CDCl_3$, δ): 154.20, 147.92, 140.89, 140.57, 133.52, 132.93, 131.85, 127.91, 125.93, 124.56, 123.26, 122.84, 121.91, 120.85, 120.47, 119.15, 119.06, 109.00, 43.24, 31.86, 29.40, 22.67, 14.12; IR (KBr): v=3051, 2956, 2922, 2850, 1624, 1597, 1469, 1381, 1330, 1259, 1234, 960, 802, 744, 727; FAB-MS (m/z): [M+H]$^+$ calcd for $C_{58}H_{67}N_4$, 819.53. found, 820.59.

Example-3

Preparation of Formula 3

A suspension of sodium hydride (12 mmol, 290 mg) in dry THF (50 mL) was added slowly to a solution of the bisphosphonate 6, tetraethyl 2,2'-bipyridine-5,5'-diylbis (methylene)diphosphonate, 912 mg, 2 mmol) and the carbazole aldehyde (5, 9-(2-(2-(2-methoxyethoxy)ethoxy) ethyl)-9H-carbazole-3-carbaldehyde) (4 mmol, 1.36 mg) in THF (50 mL). After refluxing for 12 h, at 65° C. the reaction mixture obtained was cooled followed by the removal of the THF under reduced pressure to give a yellow solid residue. The residue was suspended in water (100 mL) and extracted with dichloromethane (50 mL). The organic layer was washed with brine (50 mL) dried over $Na_2SO_4$ and concentrated to give the crude product, which was further purified by column chromatography over basic alumina using petroleum ether as eluent.

3: yield: 50%

$^1$H NMR (300 MHz, $CDCl_3$, TMS) δ (ppm): 8.81 (d, 2H, aromatic), 8.43 (d, 2H, aromatic), 8.26 (s, 2H, aromatic), 8.14 (d, 2H, aromatic), 8.03 (dd, 2H, aromatic), 7.72 (dd, 2H, aromatic), 7.47 (m, 8H, aromatic), 7.28 (2H, vinylic), 7.20 (2H, vinylic), 4.52 (t, 4H—$NCH_2$), 3.89 (t, 4H, —$OCH_2$), 3.5 (m, 12H), 3.4 (m, 4H), 3.3 (s, 6H, —$OCH_3$).

$^{13}$C NMR $CDCl_3$, (75 MHz)$_6$: 43.34, 59.00, 70.55, 71.01, 71.85, 109.17, 118.95, 120.83, 122.19, 126.01, 128.19, 131.83, 132.98, 133.51, 140.80, 141.05, 147.94, 154.24; FAB-MS: [M]$^+$ Calcd for $C_{56}H_{62}N_4O_8$, 831.01. found 832.66.

Example-4

The Zn complexes of 1 and 2 for the solid state lighting were prepares by mixing formula 1 and formula 2 with $ZnCl_2$ in 1:1 ratio with a little acetonitrile (0.5 ml) at room temperature (35° C.). The solid powder of the assays was obtained by evaporating the solvent under reduced pressure. The color of the zinc complex of assay 1 was yellow and that of assay 2 was orange in color. The powders were highly fluorescent under UV light (365 nm). The emission color of zinc complex of assay 1 was yellowish-orange and assay 2 was red under 365 nm UV light. The powder of the assays was used for coating on UV-LED.

(Formula 1A)

Zinc complex of 4,4'-bis((E)-2-(9-decyl-9H-carbazol-3-yl)vinyl)-2,2'-bipryidine

-continued (Formula 2A)

R = ——$C_{10}H_{21}$

Zinc complex of 5,5'-bis((E)-2-(9-decyl-9H-carbazol-3-yl)vinyl)-2,2'-bipryidine.

Example-5

Formula 1 shows an absorption maximum at 377 nm in chloroform. It shows an intense blue emission in hexane (419 nm) when excited at 360 nm. Which was further shifted to 467 nm in chloroform and to 472 nm in acetonitrile and DMSO with an enhancement in intensity. The increase in the quantum yield in acetonitrile ($\phi_f$=0.109) when compared to that in chloroform ($\phi_f$=0.062) is due to the decrease in nonradiative decay path way in acetonitrile. The 53 nm bathochromic shift shown by the molecule from nonpolar to polar solvents is due to the emission from the solvent relaxed state. Fluorescence decay profiles shows an increase in lifetime from hexane to acetonitrile with a monoexponential decay. Formula 2 showed a broad and red-shifted absorption band at 405 nm in chloroform, due to the increase in conjugation. Formula 2 shows a gradual and large solvatochromism in nonpolar to polar solvents. Formula 2 shows an emission maximum at 430 nm in hexane when excited at 395 nm which was further shifted to 513 nm in DMSO. This is a clear indication of excited state intraligand charge transfer. The monoexponential decay excited state lifetime of 2 gradually increase from hexane (0.81 ns) to DMSO (1.59 ns).

Figure 2:
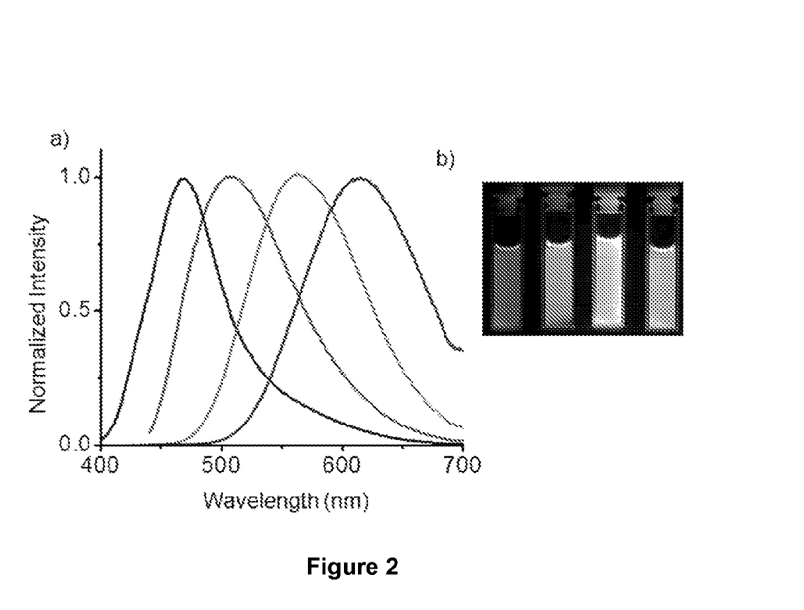
FIG. 2: shows emission spectral changes of 1 (–), 2 (–), 1.$Zn^{2+}$ (–), and 2.$Zn^{2+}$ (–) in (Conc. $6\times10^{-6}$ M in 1:1 $CHCl_3$/Acetonitrile, ex@ absorption maximum). b) Photographs showing the emission color changes.

The formula 1 and 2 are structurally similar except the linking position of donor to the acceptor. In formula 1 the donor group (carbazole) is connected to bipyridine at the 4,4'-position, but in the case of formula 2 it is connected to the 5,5'-position. In both the cases the acceptor is a good metal chelator, hence binding of metalions can also make significant changes in the photophysical properties of formula 1 and 2. The absorption band of formula 1 was shifted to 416 nm upon binding with Zn(ClO$_4$)$_2$. Corresponding changes was also observed in emission properties. The emission maximum was shifted to 563 nm from 468 nm (blue to yellow) (FIG. 2). The binding decreased the nonradiative decay path way of the excited state. The solution state quantum yield of the zinc complex of formula 1 was found to be 0.49 (rhodamine B as the standard) which was initially showing a quantum yield of 0.109 in acetonitrile. In the case of formula 2 the absorption was shifted to 452 nm and emission to 615 nm from 507 nm (green to orange) (FIG. 2) upon complexation with Zn(ClO$_4$)$_2$. Assay 2 has a quantum yield of 0.62 in acetonitrile. The complex shows a fairly good quantum yield of 0.304 in solution. Both the cases shows a 1:1 metal-ligand complex.

The red-shift in the absorption and emission wavelength of formula 2 is due to the more effective conjugation in formula 2 when compared to formula 1. The complexation of 1 and 2 with $d^{10}$ metal ions like $Zn^{2+}$ will enhance the intraligand charge transfer (ILCT). This will further shift the absorption and emission to higher wavelength, when compared to the free ligands formula 1 and 2.

Example-6

Figure 3:
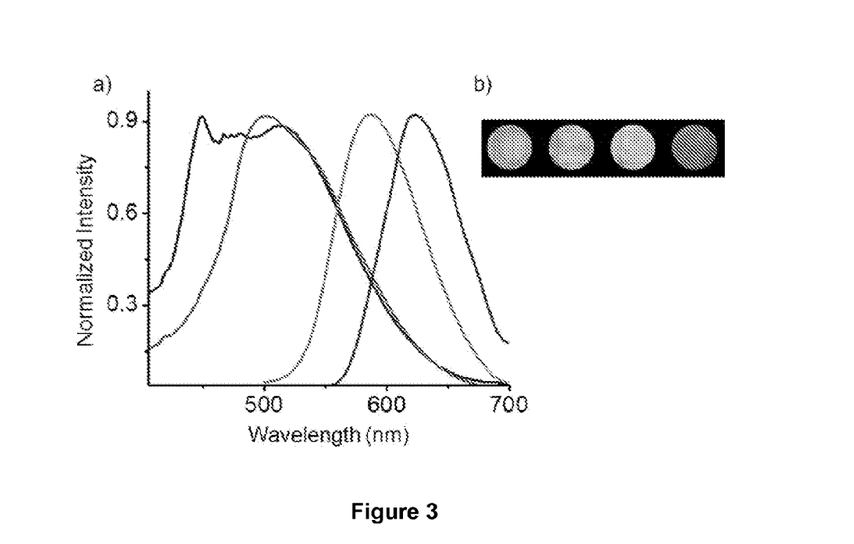
FIG. 3: demonstrate the a) Solid state emission spectral changes of 1 (–), 2 (–), 1.$Zn^{2+}$ (–), and 2.$Zn^{2+}$ (–). b) Photographs of corresponding emission color changes.

Solid state lighting needs the chromophore which emits in the solid state. Most of the molecules shows self quenching of fluorescence in solid state. This problem preclude these molecules from a practical application. The molecules described here are highly solid state emitting. The molecule with high solid state emission was utilized for the detection of zinc ions in aqueous condition. Reference can be made to: Ajayaghosh et al. PCTIN2008000374, S. Sreejith, K. P. Divya and A. Ajayaghosh, Chem. Commun., 2008, 2903. Here the carbazole appended fluorophores show fairly good quantum yield in the solid state which was measured by absolute method (integrated sphere method). The formula 1, 2 and their Zinc complexes showed slight red shift in their emission maximum. (FIG. 3) in the solid state. The formula 1 has blue emission with a quantum yield of 0.149 and its $Zn^{2+}$ has yellow emission with quantum yield of 0.086. Formula 2 has green emission with quantum yield of 0.456 and the $Zn^{2+}$ complex of formula 2 has red emission with a quantum yield of 0.043.

The assay 1 The photophysical parameters in solid state as well as the solution state are given in table 1.

Example-7

Figure 4:
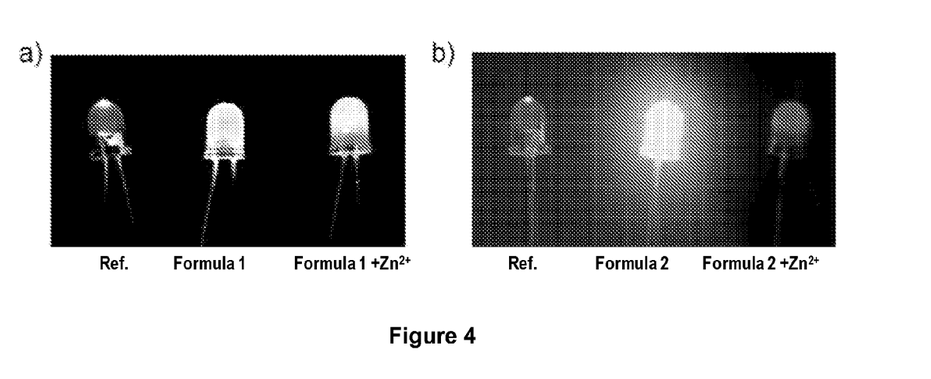
FIG. 4: shows the a) (1) A UV-LED (365 nm) illuminating blue light (commercially available from nitride semiconductors co., Ltd.), (2) LED illuminating a coated layer of 1, (3) LED illuminating a coated layer of 1.$Zn^{2+}$ complex. b) (1) A UV-LED (365 nm) illuminating blue light (2) LED illuminating a coated layer of 2, (3) LED illuminating a coated layer of 2.$Zn^{2+}$ complex.

FIG. 4 shows emission in the entire visible range (blue to red) from the fluorophore coated LED's. We purchased commercially available UV-LED's (365 nm, 20 mA) from Nitride semiconductors co., Ltd. The UV-LED when coated with compound 1, 2 and their metal complexes emit light in the entire visible region. Formula 1 and 2 are melted by heating in a mortar at 200° C. The solid melt was coated over UV LED and allowed to cool for 20 minutes. Now the LED is ready for lighting. The melts of zinc bound formula 1 and 2 are also coated on the UV LED in the same way.

Example-8

Figure 1:
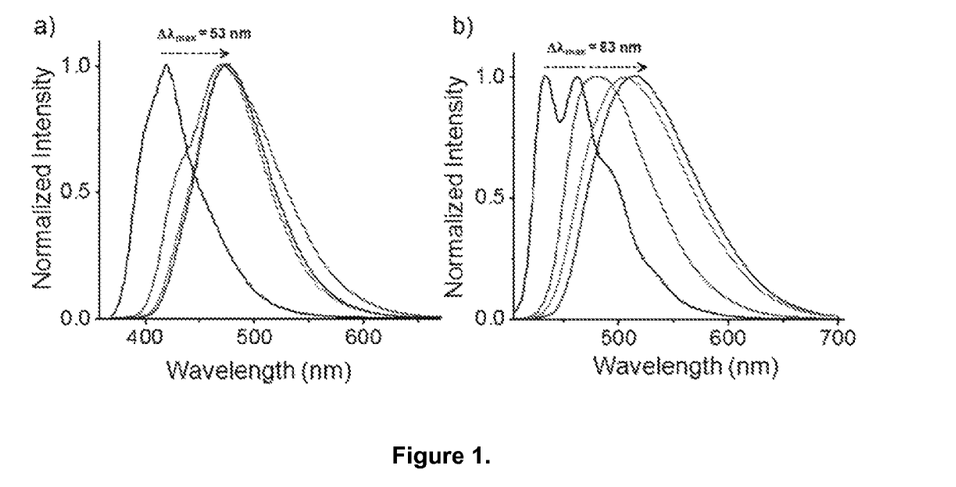
FIG. 1: shows the emission spectral changes of a) 1 [$6\times10^{-6}$ M, $\lambda_{ex}$=358 nm] b) 2 [$6\times10^{-6}$ M, $\lambda_{ex}$=395 nm] in hexane (–), $CHCl_3$ (–), acetonitrile (–), DMSO (–). Formula 1: shows the molecular structure of the ligand 1-3.

The emission spectrum of formula 2 showed large dependency on solvent polarity. In hexane a structured emission spectrum was obtained with emission maximum at 433 nm (C=6×10$^{-6}$ M, $\lambda_{ex}$=400 nm). In chloroform, the emission spectrum showed a maximum at 476 nm and become broader and shifted to longer wavelength region in acetonitrile ($\lambda_{em}$=505 nm) and DMSO ($\lambda_{em}$=515 nm) with an emission color change from blue to green (FIG. 1b). This large solvatochromism in emission shown by formula 2 could be due to the stabilization of the charge transfer state in the excited state. Since the excited state is polar in nature, will be more stabilized in polar solvents. This is further proved by the time resolved fluorescence lifetime studies. The molecule is highly emissive in less polar solvent like chloroform and showed a quantum yield of 87% (quinine sulphate in 0.1 N H$_2$SO$_4$ as standard) while emission intensity decreased in acetonitrile ($\phi_f$=69%).

Figure 5:
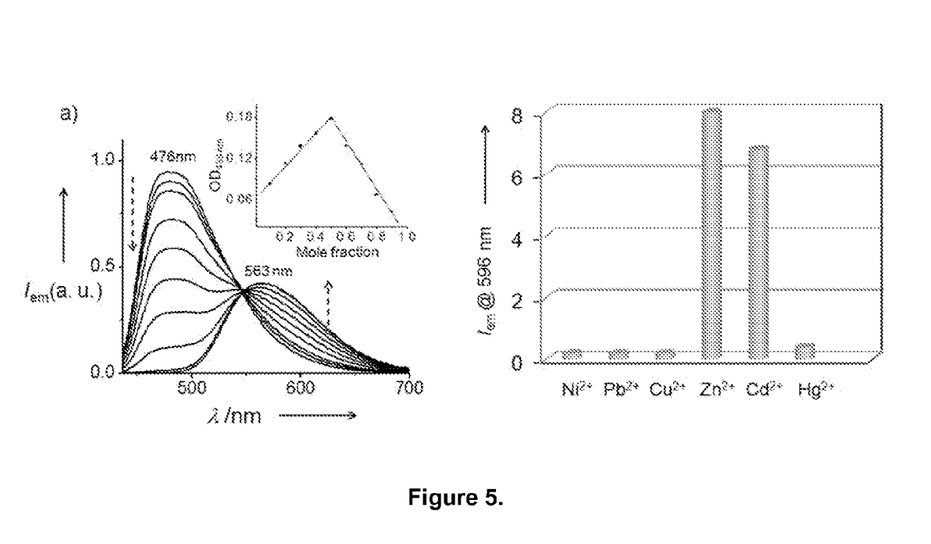
FIG. 5: demonstrate the a) Emission spectral response of 2 ($6\times10^{-6}$ M) in chloroform upon addition of $Zn(NO_3)_2$ (0-1 eqv.). Inset figure shows the Job's plot showing the 1:1 binding of 2 to $Zn(NO_3)_2$. b) Plot of fluorescence intensity of 2 (6 M) monitored at 596 nm with different metal ions.
Figure 6:
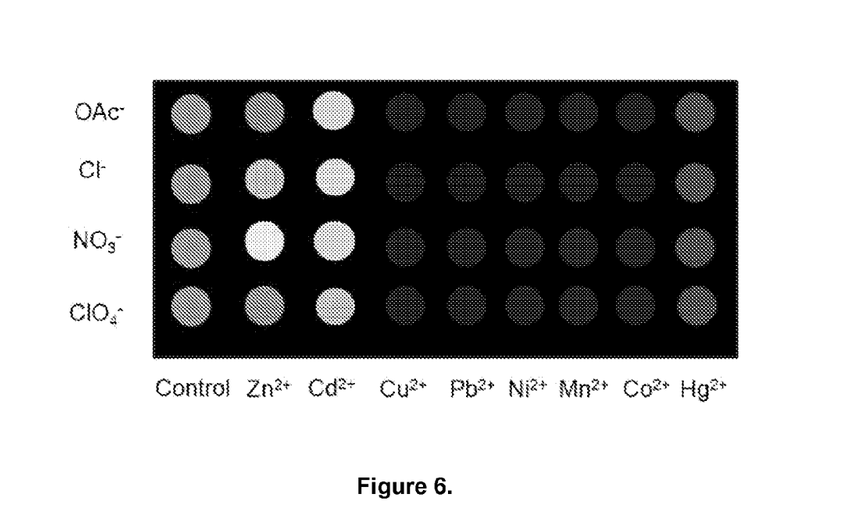
FIG. 6: a) Color change profile of formula 2 ($6\times10^{-6}$ M) upon addition of metal salts with different counteranions in chloroform (fluorescence output from a BioTek cell reader, $\lambda$ex@ 435 nm).
Figure 7:
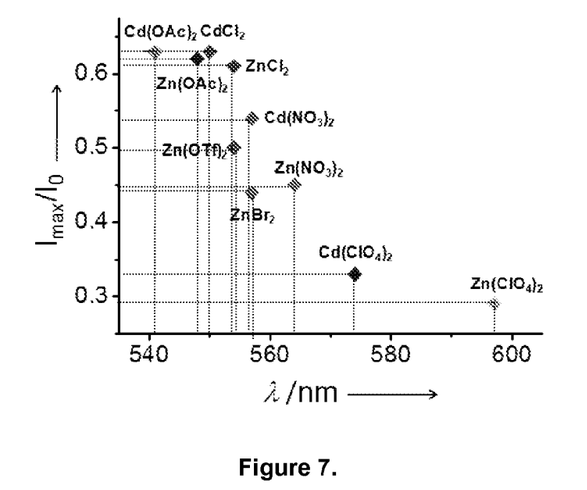
FIG. 7: Fluorescence intensity versus wavelength based recognition of metals salts with formula 2.
Figure 8:
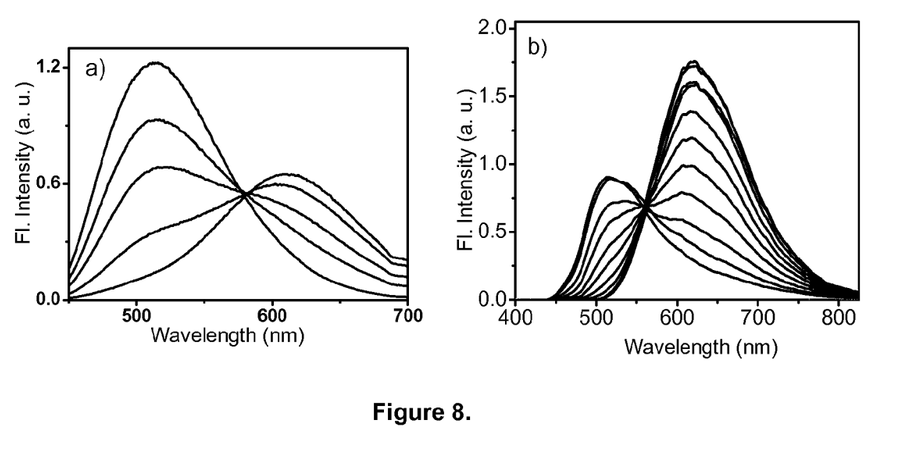
FIG. 8: showing the a) one photon and b) two photon fluorescence emission spectra for the titration of 3 [(a) Conc. $6\times10^{-6}$ M (b) Conc. $6\times10^{-5}$ M in acetonitrile solution] with $Zn(ClO_4)_2$ in acetonitrile
Figure 9:
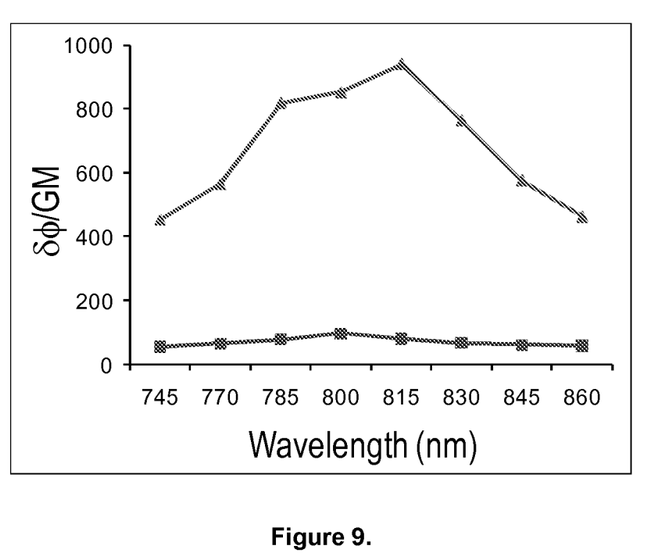
FIG. 9: shows Two-photon action spectra of 3 ($6\times10^{-5}$ M in acetonitrile solution) in the absence (■) and presence (▲) of $Zn^{2+}$.
Figure 10:
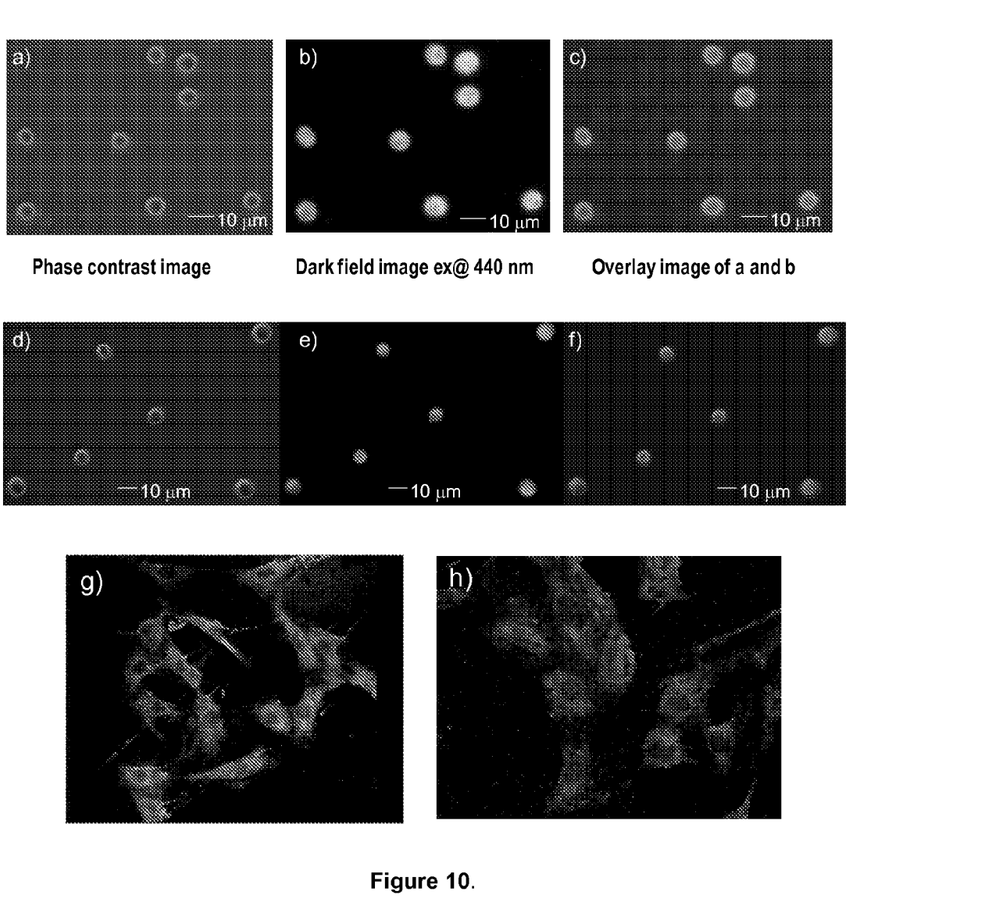
FIG. 10: a-f shows the fluorescence image of C2C12 (Mouse myoblast cells) with 3 before (a-c) and after (d-f) $Zn^{2+}$ incubation. Two photon microscopic images of HeLa cells with 3 before (g) and after (h) $Zn^{2+}$ incubation FIG. 11. Scheme of synthesis of formula 1, 2 and 3
Figure 11:
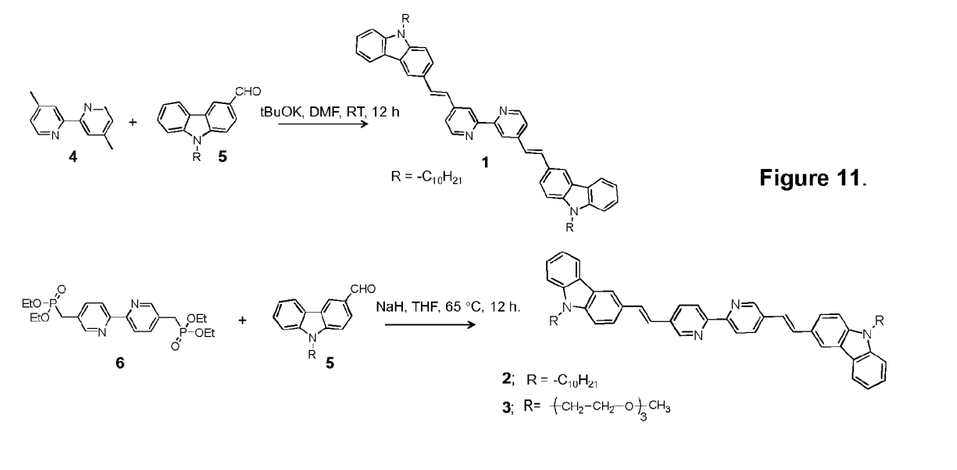

Addition of transition metal salts to a solution of formula 2 (6×10$^{-6}$ M) in chloroform showed a significant decrease in the absorption band at 405 nm with the concomitant formation of a new red-shifted band at around 460 nm. The new band indicate the planarization of the metal bound fluorophore and also the decrease in the HOMO-LUMO gap due to the stabilization of the LUMO on metal binding. The emission of formula 2 at 476 nm was significantly quenched by different transition metal ions except zinc (II) and cadmium (II). In the case of Zn$^{2+}$ the emission band at 476 nm was quenched with a concomitant formation of a new red-shifted band. For example, the fluorescence response of formula 2 in chloroform against Zn(NO$_3$)$_2$ is shown in FIG. 5a. Upon titration of Zn(NO$_3$)$_2$ The emission maximum is gradually decreased with concomitant formation of a new band at 563 nm through an isoemissive point at 547 nm. The individual emission response of formula 2 against different transition metal ions is shown in FIG. 5b. The selectivity was checked by recording the fluorescence of formula 2 in presence of 5 times excess of different cations. Surprisingly we found that the red-shifted emission of 2+Zn$^{2+}$ was strongly dependent upon the counteranion of the zinc salt. The individual emission response of formula 2 with various zinc salts showed a remarkable change (FIG. 6). This observation further extended our investigation to find out the ability of formula 2 to discriminate zinc (II) ions with various counteranions. The emission peak of formula 2 in chloroform ($\lambda_{em}$=476 nm) was red-shifted to 597 nm on binding with Zn(ClO$_4$)$_2$ with a quantum yield of 0.30. The emission peak was blue shifted in the case of Zn(OAc)$_2$ ($\lambda_{em}$=548 nm, $\phi_f$=0.50) in comparison with ZnCl$_2$ ($\lambda_{em}$=554 nm, $\phi_f$=0.50) and Zn(NO$_3$)$_2$ ($\lambda_{em}$=563 nm, $\phi_f$=0.40). The large shift in the emission maximum depending on the couteranion is due to the different coordinating ability between the counteranion and zinc (II). The net charge quantities of zinc cations depend on the average distance between zinc cations and counteranion, which is determined by the ionization coefficient of the zinc salt in solution. Zinc (II) may possess more net charge in the case of ClO$_4$$^-$ as the counteranion due to the larger ionization equilibrium coefficient of Zn(ClO$_4$)$_2$ in solution. Because of the more covalent bond property of Zn(OAc)$_2$, the net effective charge on zinc (II) will be low. The Job plot revealed a 1:1 complexation between the fluorophore and the Zn$^{2+}$ in all cases. The binding constants calculated from Benesi-Hildebrand plots shows that the binding constant is highest for Zn(ClO$_4$)$_2$ (3.33×10$^5$ M$^{-1}$) and it decreases from Zn(NO$_3$)$_2$ (1.47×10$^5$ M$^{-1}$) to ZnCl$_2$ (7.8×10$^4$ M$^{-1}$); Zn(OAc)$_2$ shows the lowest value (1.77×10$^4$ M$^{-1}$) in chloroform. The possibility to monitor two emission maxima with a single wavelength excitation makes formula 2 as an efficient ratiometric probe for various zinc (II) salts (FIG. 7). The variation in the fluorescence properties is not observed in the case of non-binding metal salts with different counterions. For example, we have checked the effect of various sodium salts like perchlorate, nitrate, chloride and acetate. But shows no variation in the fluorescence property of formula 2.

The detailed photophysical properties of the formula 2 on complexing with various zinc salts are summarized in table 2. The stabilization of the excited state is maximum in the case of Zn(ClO$_4$)$_2$ complex. It gradually decreases as the ionization of the zinc complex decreases. This is clear from the quantum yield and lifetime values of 2.Zn$^{2+}$ complexes. The effective discrimination of various zinc salts is accomplishable by using the probe formula 2 since the excited state of formula 2 is CT state. So that the fluorescence can be easily perturbed by the stabilization of excited state.

Example-9

Screening of the counteranions can be done by recording the emission color of formula 2 in the presence of different metal salts using a BioTeck cell reader upon excitation at 435 nm (FIG. 6). Control experiment in the absence of any metal salts showed the original blue fluorescence of the probe formula 2. The plot of fluorescence intensity versus wavelength can apply for the determination of metal salts which are not easy to find out by visual color change (FIG. 7). The changes in emission properties are highly solvent dependent. For example, the emission shift of formula 2 on binding with various zinc salts in acetonitrile is negligible. Since the emission of formula 2 arises from the stabilized charge transfer state, the counteranion effect is negligible in acetonitrile. The quantum yield of 2.Zn$^{2+}$ complex was nearly the same in acetonitrile ($\phi_f$=0.30, rhodamine B in ethanol as standard) irrespective of the counteranion whereas in chloroform the quantum yield was dependent on the counteranions (Table 2).

Example-10

Formula 3 has an absorption maximum at 406 nm in acetonitrile. It shows an emission maximum at 510 nm in acetonitrile upon excitation at 390 nm. The emission maximum was shifted to 525 nm in 1:1 acetonitrile/water, without significant shift in the absorption maximum. The emission maximum was red-shifted to 611 nm upon addition of 1 equivalent of ZnCl$_2$ to solution of formula 3 in acetonitrile or 1:1 acetonitrile/water. The emission intensity of zinc complex of formula 3 was reduced upon excitation at 440 nm compared to free formula 3.

Formula 3 was showing two photon absorption (TPA) cross section value of 107 GM at 800 nm. Interestingly the Zn$^{2+}$ complex of formula 3 shows a 12 fold enhancement in the TPA cross section in acetonitrile solution. Two photon excitation at 860 nm produced ratiometric emission spectra with a red-shifted emission maximum for formula 3 on binding with Zn$^{2+}$. The two photon excited fluorescence spectra shows an enhancement in the emission intensity for 3.$Zn^{2+}$ complex when comparing to free formula 3. This is in contrast to the steady state fluorescence behaviour, where coordination with $Zn^{2+}$ decreases the fluorescence intensity. This indicates that coordination with $Zn^{2+}$ result in significant enhancement in the two photon excited fluorescent (TPEF) signal along with the increase in the TPA cross section.

The two photon excitation was carried out using a mode locked femtosecond Ti: sapphire laser from Spectra Physics (Tsunami), with a repetition rate of 82 MHz and a pulse width of about 100 femtoseconds. The tuning range of the Ti-Sapphire laser is 690 nm to 1080 nm. The output laser beam, with an average power of 0.6-0.8 W, is vertically polarized.

Example-11

The two photon microscopic images of HeLa cells labeled with formula 3 showed bright TPEF. The cells incubated with $Zn^{2+}$ when imaged with formula 3 showed an enhanced TPEF at 595-640 nm. So formula 3 can be used as an efficient fluorescent molecular probe for selective detection of intracellular free $Zn^{2+}$ ions in living cells by two photon microscopic imaging.

The Main Advantages of the Present Invention are:

1) A clever design of donor-acceptor-donor based fluorophore and their positional modification and metal ion binding assisted the solid state lighting in the entire visible region. The combination of change in linking position and metal complexation helped to attain full color tenability in the visible region. Here, we have successfully demonstrated the conversion of UV light into visible light by coating the fluorophores on 365-nm emitting LED. Thus with a blue emitting LED we could obtain the entire visible spectrum such as blue, green, orange and red.

2) The excited state charge transfer property of the fluorescent probe formula 2 is successfully utilized for the effective screening of transition metal salts with different counteranions. The easy synthesis, high sensitivity and selectivity of the present probe make it a potential candidate for the discrimination of transition metal salts. The present probe can be employed for the selective visual sensing of zinc salts with various counterions in analytical samples.

3) Formula 3 can be used as an efficient ratiometric fluorescent molecular probe for selective detection of intracellular free $Zn^{2+}$ ions in living cells by two photon microscopic imaging.

We claim:

1. A carbazole end capped bipyridine compound of formula A

General formula A $R = C_{10}H_{21}$

2. The carbazole end capped bipyridine compounds as claimed in claim 1, wherein the structural formulae of the representative compounds are:

1

$R = \text{---} C_{10}H_{21}$ 4,4'-bis((E)-2-(9-decyl-9H-carbazol-3-yl)vinyl)-2,2'-bipyridine.

-continued

R = —C$_{10}$H$_{21}$ 5,5′-bis((E)-2-(9-decyl-9H-carbazol-3-yl)vinyl)-2,2′-bipyridine.

* * * * *